United States Patent [19]

Panitz

[11] Patent Number: 5,410,256

[45] Date of Patent: Apr. 25, 1995

[54] DISSIPATION FACTOR AS A PREDICTOR OF ANODIC COATING PERFORMANCE

[75] Inventor: Janda K. G. Panitz, Edgewood, N. Mex.

[73] Assignee: Sematech, Inc., Austin, Tex.

[21] Appl. No.: 95,457

[22] Filed: Jul. 20, 1993

[51] Int. Cl.⁶ .................. G01R 25/00; G01N 17/00
[52] U.S. Cl. ........................... 324/683; 324/71.1;
324/663; 204/434; 205/81; 427/8
[58] Field of Search ............... 324/663, 650, 651, 671,
324/674, 681, 683, 71.1, 71.2, 544, 551; 427/8,
9; 204/434, 153.1; 205/81

[56] References Cited

U.S. PATENT DOCUMENTS

| | | | |
|---|---|---|---|
| 3,230,449 | 1/1966 | Kaiser | 324/679 |
| 3,458,803 | 7/1969 | Maguire | 324/679 |
| 3,866,117 | 2/1975 | Erdman | 324/514 |
| 3,975,681 | 8/1976 | Angelini et al. | 324/71.1 |
| 5,243,298 | 9/1993 | Runner | 324/71.1 X |

*Primary Examiner*—Kenneth A. Wieder
*Assistant Examiner*—Diep Do
*Attorney, Agent, or Firm*—William W. Kidd

[57] ABSTRACT

A dissipation factor measurement is used to predict as-anodized fixture performance prior to actual use of the fixture in an etching environment. A dissipation factor measurement of the anodic coating determines its dielectric characteristics and correlates to the performance of the anodic coating in actual use. The ability to predict the performance of the fixture and its anodized coating permits the fixture to be repaired or replaced prior to complete failure.

10 Claims, 2 Drawing Sheets

| TEST SAMPLE | 1 KHz | 10 KHz | 100 KHz | 1 MHz | PERFORMANCE |
|---|---|---|---|---|---|
| B | 0.175 | 0.0789 | 0.0442 | 0.0338 | UNACCEPTABLE |
| C | 0.151 | 0.0894 | 0.0541 | 0.0314 | UNACCEPTABLE |
| D | 0.0974 | 0.0479 | 0.0305 | 0.0238 | UNACCEPTABLE |
| E | 0.0785 | 0.0418 | 0.0305 | 0.0338 | 4000 MINUTES OF USE |
| A | 0.0718 | 0.0409 | 0.0276 | 0.0207 | 7000 MINUTES OF USE |

DISSIPATION FACTOR AS A PREDICTOR OF ANODIC COATING PERFORMANCE

The United States Government has rights in this invention pursuant to Contract No. DE-FI04-89-AL58872 between the Department of Energy and SEMATECH.

BACKGROUND OF THE INVENTION

1. Field of the Invention

The present invention relates to the field of semiconductor manufacturing tools and, more specifically, to the performance of anodic coatings on etching tools.

2. Prior Art

It is well-known in the semiconductor industry to utilize protective coatings on tools and fixtures in order to extend their useful life. Anodic aluminum oxide coatings are frequently formed on fixtures used in plasma-assisted etching systems commonly employed to fabricate integrated circuits. Anodic coatings display many desirable characteristics, including: producing a range of plasma potentials suitable for controlling the degree of anisotropic versus isotropic etching; shaping stable, uniform, reproducible plasmas which result in stable, uniform and reproducible etch rates; retarding etching of an underlying metal substrate, thereby protecting against the introduction of metal species from a fixture into the etch gas chemistry where these metal species may alter the etch rate, as well as contaminating the wafer or devices formed on the wafer; slowing fixture erosion which can lead to dimensional changes that could, in turn, result in gas flow variations and/or poor seals; and forming a relatively dense, smooth, strong, temperature resistant, low vapor pressure material which typically reduces vacuum "pump-down" time and particulate generation to levels conducive to commercial wafer fabrication practices.

Although beneficial properties of anodic coatings are well known and practiced, in general, it is difficult to determine whether an as-anodized coating will perform satisfactorily during the lifetime recommended by the equipment manufacturer; fail prematurely, whereby interrupting maintenance and production schedules, as well as undesirably processing a number of wafers before the problem is discovered and corrected; or never respond in a satisfactory fashion to an etch environment during the initial fixture or tool "prove-in" period that is typically necessary to achieve useful, stable reproducible etch rates, which can ultimately impact and disrupt production.

It is appreciated that some technique for determining the deterioration or erosion rate of a given anodic coating prior to actual failure would be of considerable benefit, as well as aid in the prevention of the destruction of wafers or interruption of production cycles. It would be of a greater benefit, if prior to use a given anodic coating can be tested to determine its useful life. Such a predictive process can be implemented at an early stage (for example, as an initial acceptance test of a fixture/tool), to predict with certain accuracy the coating response, stability, longevity and usefulness of the anodic coating when used in plasma assisted etch environments.

Accordingly, it is an object of the present invention to use a dissipation factor measurement to predict the performance properties of an anodic coating.

SUMMARY OF THE INVENTION

A dissipation factor measurement as a predictor of anodic coating performance in etching systems is described. In order to determine performance characteristics of an anodic coating on a semiconductor fixture, a dielectric property of the anodic coating is measured. A capacitance meter is coupled to the fixture and a capacitive response, in the form of a dissipation factor measurement, is noted. The dissipation factor reading at lower frequencies is indicative of the dielectric property of the coating and is a reliable predictor for determining the performance of the coating.

In order to couple the capacitance meter to the anodic coating, a counter-electrode is used to attach an electrical lead. A variety of counter-electrode materials are available depending on the physical parameters encountered. Vacuum deposited metal films, conductive paints, metal coatings formed by electroless deposition processes, metal foils and mercury (drops) are materials which can be used as counter-electrodes. Alternatively, "non-conducting" probes employing antennae, wave guides or tuned cavities can be utilized.

Generally, the technique of the present invention is used to determine the performance, such as its useful life under set conditions, prior to actual use of the fixture in an etching environment. The prediction of the performance of the anodic coating will permit the fixture to be repaired or replaced prior to complete failure. In an alternative scheme, the technique of the present invention is utilized to provide periodic measurements after the fixture has been installed in an etching system.

DETAILED DESCRIPTION OF THE PREFERRED EMBODIMENTS

A dissipation factor measurement as a predictor of anodic coating performance in an etching system is described. In the following description, numerous specific details are set forth, such as specific devices, measuring techniques, materials, etc., in order to provide a thorough understanding of the present invention. However, it will be obvious to one skilled in the art that the present invention may be practiced without these specific details. In other instances, well-known processes and structures have not been described in detail in order not to unnecessarily obscure the present invention.

The present invention provides for a technique in which dissipation factor measurements can be readily adapted to predict the behavior of anodic coatings on fixtures and/or tools (for simplicity, all fixtures, tools, devices, etc. will be collectively referred to herein as fixtures) when subjected to a plasma-assisted etching system, such as an electron cyclotron resonance (ECR) plasma etcher or reactive ion etching (RIE) system. Prediction techniques can be implemented at acceptance testing of a given anodized fixture in order to establish its performance characteristic or useful life prior to actual use. Alternatively, such prediction techniques can be utilized during various periods during use in order to continually measure and estimate the present performance or remaining life of the fixture.

The scheme for prediction of anodic coating performance in the present invention is achieved by determining a dielectric property of the particular anodic coating. By measuring this dielectric property of an anodic coating, a correlation can be established to various performance values. Although a variety of measurement techniques for measuring dielectric properties can be used, the present invention relies on the use of the dissipation factor. Thus, the dielectric property of an anodic coating is referenced in capacitive terms and measured in terms of the dissipation factor.

Figures 1, 4:
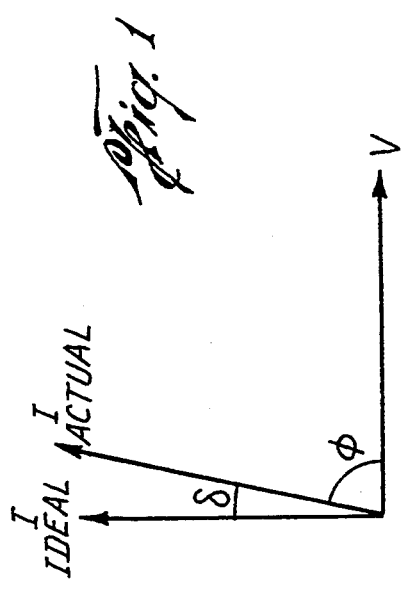
FIG. 1 is a graphical illustration showing phase and loss angles associated with a capacitive circuit.
FIG. 4 is a table showing one experimental result for utilizing dissipation factor measurements to practice the present invention.

Referring to FIG. 1, a voltage-current diagram for a capacitive circuit is shown. In an ideal capacitor, current I leads voltage V by a phase angle of 90 degrees. However, in an actual capacitor, I leads V by an angle less than 90 degrees. This angle is defined as the phase angle and denoted by $\phi$. The difference from the ideal angle of 90 degrees is the loss angle, which is denoted by $\delta$. The loss angle signifies the amount of loss in a capacitor due to a resistive component, which is typically the series resistance present in the capacitor.

One term for expressing this power loss is the power factor. The power factor (pf) expresses the loss in a capacitor when AC voltage is applied. The power factor is identified with the phase angle $\phi$ and given by:

$$pf = R/Z = \cos \phi \qquad \text{(Equation 1)}$$

where R is the equivalent series resistance and Z is the impedance, determined by the vector sum of R and the capacitive reactance Xc.

Another measure of determining loss is by measuring the dissipation factor of the capacitor when an AC voltage is applied. The dissipation factor (df) is identified with the loss angle $\delta$ and given by:

$$df = R/Xc = 2\pi f CR = \tan \delta \qquad \text{(Equation 2)}$$

where R is the equivalent series resistance, C is the capacitance and f is the frequency in hertz.

It should also be noted that other formulae are available for determining the dissipation factor. Furthermore, for pf values of less than 10%, the pf value and the df value are practically equal. Thus for low-loss dielectrics, either the pf or the df values would give essentially the same result. However, for simplicity, only the dissipation factor (df) is measured and discussed in describing the technique of the present invention. Accordingly, the below description addresses the measurement of the dissipation factor of an anodic coating to determine its dielectric properties for the purpose of predicting the performance of the particular anodic coating.

Figure 2:
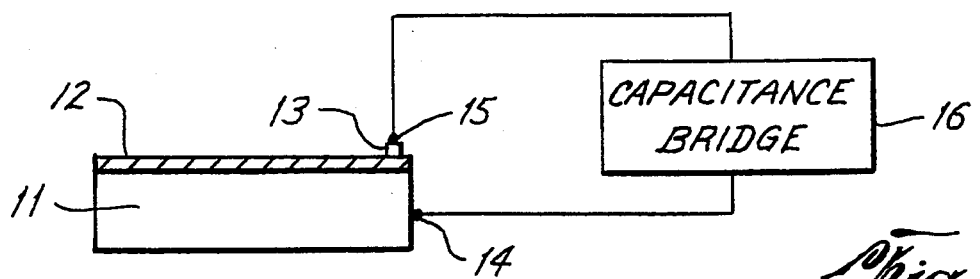
FIG. 2 is a schematic diagram showing a coupling of a capacitance bridge to an anodized fixture to measure its dissipation factor in the practice of the present invention.

Referring to FIG. 2, a fixture 11 for use within an etching environment is shown. Fixture 11 is typically manufactured from a metallic material and has an anodic coating 12 upon one surface. In this particular example, fixture 11 is formed from an aluminum alloy and aluminum oxide ($Al_2O_3$) is utilized as anodic coating 12. It is to be appreciated that a variety of well known metallic materials and anodic coatings which are utilized for etch applications can be readily substituted. Furthermore, it should be noted that many fixtures for use in etching systems are completely anodized on all exposed surfaces and the particular fixture 11 in FIG. 1 is provided as an example only.

It has been shown through experimentation that the performance characteristics of an anodic coating is related to its dielectric properties. Although a variety of techniques are available for measuring dielectric properties, the dissipation factor is used as the measure of the dielectric property in the practice of the present invention.

In order to measure the dissipation factor, a capacitance measuring device in the form of a capacitance bridge 16 is coupled to fixture 11. One terminal 14 of the bridge is coupled to the aluminum alloy (substrate metal) itself. The other terminal 15 is coupled to a counter-electrode 13, which then is coupled to the exposed side of anodic coating 12. Thus, the capacitance bridge 16 is coupled across a substrate metal (fixture)/anodic coating/counter-electrode structure. Then, the bridge 16 is utilized to measure angle $\delta$ to determine the dissipation factor of the fixture/anodic coating/counter-electrode structure. A counter-electrode 13 is necessary because in order to effectively attach terminal 15 to the coating 12. A variety of well-known measurement devices can be readily used to measure the dissipation factor (or the loss angle). For example, the particular capacitance meter used to obtain measurements noted in the table of FIG. 4 utilized Capacitance Meter Model 4278, which is manufactured by Hewlett-Packard Company.

Figure 3:
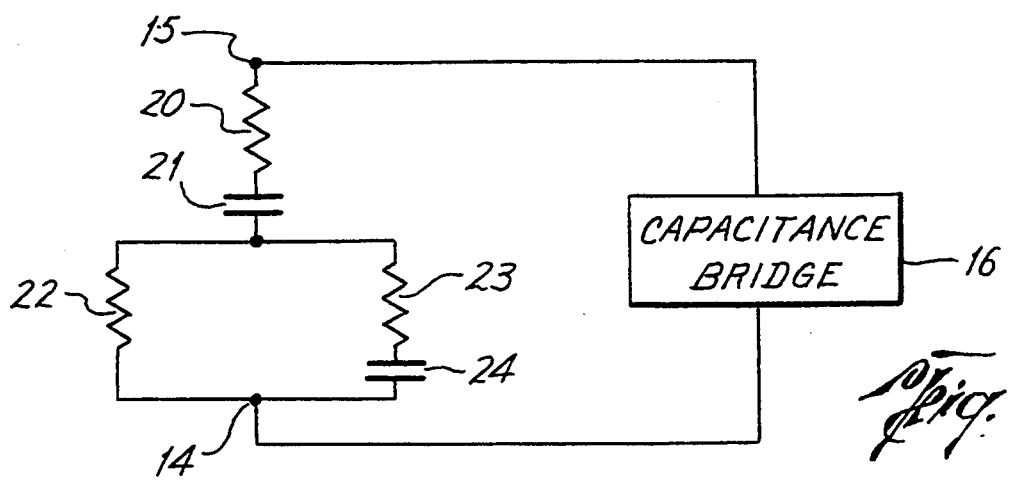
FIG. 3 is a schematic diagram showing an equivalent circuit for the diagram of FIG. 2.

Also referring to FIG. 3, an equivalent circuit diagram for the fixture/coating/counter-electrode structure is shown. The counter-electrode 13 is represented by the series combination of resistor 20 and capacitor 21. Resistor 20 denotes the resistance of the counter-electrode 13, while capacitor 21 denotes the capacitance between the counter-electrode 13 and the anodic coating 12.

The anodic coating 12 is represented by the combination of resistor 22 in parallel to the series combination of resistor 23 and capacitor 24. These three components 22–24 represent the impedance due to the coating structure and composition. Thus, an analysis performed by the capacitance bridge 16 is the measurement of the response of the equivalent circuit to an applied AC voltage generated by the capacitance bridge 16.

By experimentation, it has been shown that a direct correlation exists between the measured dissipation factor of a particular anodic coating and its performance characteristic. Specifically, a variety of aluminum oxide anodic coatings of different thicknesses were formed on an aluminum fixture and utilized in the experiments. A particular type of counter-electrode was selected for each set of samples of the experiment (actually, several counter-electrodes were coupled to each sample in order to obtain more than one reading from each sample). The samples were stored at ambient relative humidity of 18–22% for consistency.

The dissipation factor of each coating 12 was then measured utilizing the capacitance bridge configured as in FIG. 2. The readings were taken at an ambient relative humidity of 18–25% and at an ambient temperature of 25–30 degrees C. Furthermore, the dissipation factor measurements were taken at various frequencies.

Subsequently, the sample fixtures with the anodic coatings were each subjected to the same etching process to measure the erosion rate of each of the coatings. A result of an experiment is shown in the table of FIG. 4. From the experimentation, a correlation between the dissipation factors at the lower frequency (1 KHz and 10 KHz) and coating erosion rates in the etch system are noted.

In the particular example, two of the samples (E and A) exhibited acceptable performances by withstanding a substantial number of minutes of use under an etching condition. Three of the samples were not usable or were usable for a relatively short time. By observing the results of FIG. 4, a minimum acceptable criterium for anodic coatings can be selected for the particular coating and substrate combination. It can be extrapolated from the table that a dissipation factor of 0.0420 at 10 KHz can be specified as the acceptable upper criterium for the noted combination of coating and substrate material. Thus, in this particular example, samples E (df=0.0418 at 10 KHz) and A (df=0.0409 at 10 KHz) would be acceptable, but samples B, C and D (df=0.0789, 0.0894, 0.0479 at 10 KHz, respectively) would not be acceptable.

The identification of a maximum dissipation factor value at a given test frequency for a given substrate material and coating combination, provides for an establishment of a minimum acceptable level for a particular etching process. An advantage of knowing the performance characteristic based on the dissipation factor, allows for a prediction of how a particular coating will perform under actual etch conditions.

By using this prediction technique, the shortcomings noted in determining the performance of an as-anodized (anodic) coating can be determined prior to actual use. Accordingly, statistical life expectancy of an as-anodized coating can be assessed prior to use; grossly undesirable coatings can be identified without the need for subjecting the as-anodized coating to conditioning periods; and premature failure of the coating during actual wafer processing can be prevented.

Furthermore, the ability to predict the performance of a particular anodic coating, essentially provides for a technique to benchmark its performance characteristics. Thus, a manufacturer of a tool or fixture can readily subject it to a number of performance tests (for example, in various operating or ambient environments, etching gases, RF power levels and frequency) to determine the performance response for a given dissipation factor. This performance benchmark can then be used to provide acceptance criteria for the user of the tool or fixture.

In the practice of the present invention, it is appreciated that the performance prediction of a particular anodic coating is based on its dissipation factor. Generally stated, the lower the dissipation factor for a particular coating, more desirable is the performance characteristic. In reference to the equivalent circuit of FIG. 2, more desirable performance is achieved when the circuit approaches an ideal capacitor. That is, when the loss angle $\delta$ approaches zero.

As is noted in the circuit diagram of FIG. 2, two equivalent capacitive components are encountered. The capacitance of interest is that value represented by device 24, which denotes the capacitive component of the anodic coating impedance. Unfortunately, the use of the counter-electrode 13 injects a second capacitive device 21. Thus, it is imperative that the placement and the coupling of the counter-electrode 13 onto the anodic coating 12 be consistent for each dissipation factor measurement taken.

In order to obtain this consistency, care must be exercised in selecting, coupling and using the counter-electrode 13. A variety of different materials can be used for counter-electrode 13. Some examples are vacuum deposited metal films, thermally evaporated metal dots (such as gold, silver and aluminum dots), conductive paint, compliant metal foil (with or without a thin polymeric coating on the contacting surface), and a drop of mercury. It is appreciated that these materials are described as examples and other materials can be readily utilized to provide the counter-electrode for practice of the present invention.

A preferred counter-electrode is the use of thermally evaporated gold dots. Gold dots having a thicknesses of 0.5 to 1.0 micron with a diameter of ⅛ to 1 inch operate effectively as counter-electrodes. It should be noted that extremely thin gold coatings may not be sufficiently mechanically robust and electrically conductive, while overly thick gold dots may experience significant intrinsic stress and partially delaminate.

Conductive paints typically are not as sensitive and accurate as the gold dots when used as counter-electrodes, but are capable of providing predictive information if care is taken with regard to the use in defined relative humidity environments. A number of conductive paints with copper, aluminum, graphite or silver particles or flakes are readily available commercially.

Metal foils with a thin layer of a polymer adhesive or wax on one side are also commercially available and can be utilized as a counter-electrode. However, variations in the dielectric properties of the adhesives can result in varying dissipation factor readings. Therefore, more care must be given to the properties of the adhesive, when foil counter-electrodes are used. Certain polymer coated or waxed metal foil counter-electrodes have a substantial advantage as counter-electrode material, because these electrodes can be applied and readily removed with little or no harmful contamination of the fixture surface.

A drop of mercury can also be placed (mechanically constrained in a stencil) on the surface for use as a counter-electrode. Due to the liquid properties of mercury, the drop of mercury flows onto the surface. When mercury is used as a counter-electrode, the surface roughness of the dielectric coating will need to be considered as a notable source of error.

The use of a particular material as a counter-electrode is a design choice dependent on a number of factors. Practical use considerations include the coating surface porosity and roughness, ambient relative humidity, past trends in the exposure to various relative humidity environments, and the range of values that can be measured with the particular capacitance measuring device in use. Alternatively, "non-contacting" probes, which can employ antennae, wave guides or tuned cavities (but not limited to these) can be readily adapted for obtaining the measurements, instead of the contacting electrode, needed for the practice of the present invention.

It should be stressed that water condensation between the counter-electrode 13 and the anodic coating 12 surface will influence the actual dissipation factor reading measured. Coatings with a rough or porous surface tend to condense water readily and, therefore, require more care with regard to counter-electrode application than smooth, dense coatings. Also, the amount of water entrained in an anodic coating is affected by its history of exposure to wet and dry environments. Normal fluctuations in the ambient relative humidity most likely will affect the measurement. High ambient humidity favors the use of strongly adhering counter-electrodes.

The presence of moisture between the counter-electrode 13 and the anodic coating 12, essentially places added series capacitance in the form of an added dielectric. Although this added series capacitance, which actually reduces the overall circuit capacitance, can be useful in desensitizing an overly high reading, the preference is to have a tight adherence of the counter-electrode to the coating in order to remove or reduce the capacitive effects of the counter-electrode.

It is to be appreciated that the dissipation factor measurements are dependent on frequency. However, it is the lower frequency dissipation factor readings which actually provide the information on coating performance. In the particular example, 1 KHz and 10 KHz are regarded as the lower frequencies, while 100 KHz and 1 MHz are regarded as higher frequencies. Generally, coatings with relatively high dissipation factors at lower frequencies perform poorly and coatings with relatively low dissipation factors at lower frequencies perform well.

In the event the dissipation factor measurements do not differ noticeably among the samples, the test environment should be reanalyzed for better adhering counter-electrodes, improved relative humidity and entrained water controls, as noted above. If low frequency dissipation factor readings are consistently out of range for the particular capacitance meter, then the set-up can be desensitized. However, as stated earlier, this is not the most preferred technique.

It has been noted in the frequency response of the test circuit that the dissipation factor readings at the higher frequencies tend to be more nearly equal in value and independent of the coating performance in an etching system. It is hypothesized from Equation 2 that the capacitance value (C) is over-shadowed by the frequency component (f) at the higher frequencies. Accordingly, the slight variations in C noted by the different coatings are less significant in the overall calculation of the dissipation factors at the higher frequencies.

However, this convergence of the dissipation factor values at the higher frequencies can still be utilized in providing some experimental control. Generally, a decrease in the dissipation factor with an increase in test frequency indicates that the fixture under test is equivalent to a circuit having a capacitor and a resistor in parallel. Alternatively, an increase in the dissipation factor with an increase in the test frequency indicates that the fixture under test is equivalent to a circuit having a capacitor and a resistor in series.

Finally, it should be stressed that the dissipation factor is dependent on a number of other parameters and care should be given when measuring the dissipation factor. These other parameter constraints include various production environment factors, such as the type of etching equipment being utilized, duty cycle, etch chemistry, feature size, wafer size and prior history of the system. Aside from the processing parameters, the actual material of the fixture and the type of anodic coating is a significant factor. However, when carefully implemented and compared against known benchmarked results, the dissipation factor measurement will predict the performance of a particular anodic coating with relative accuracy.

Figure 5:
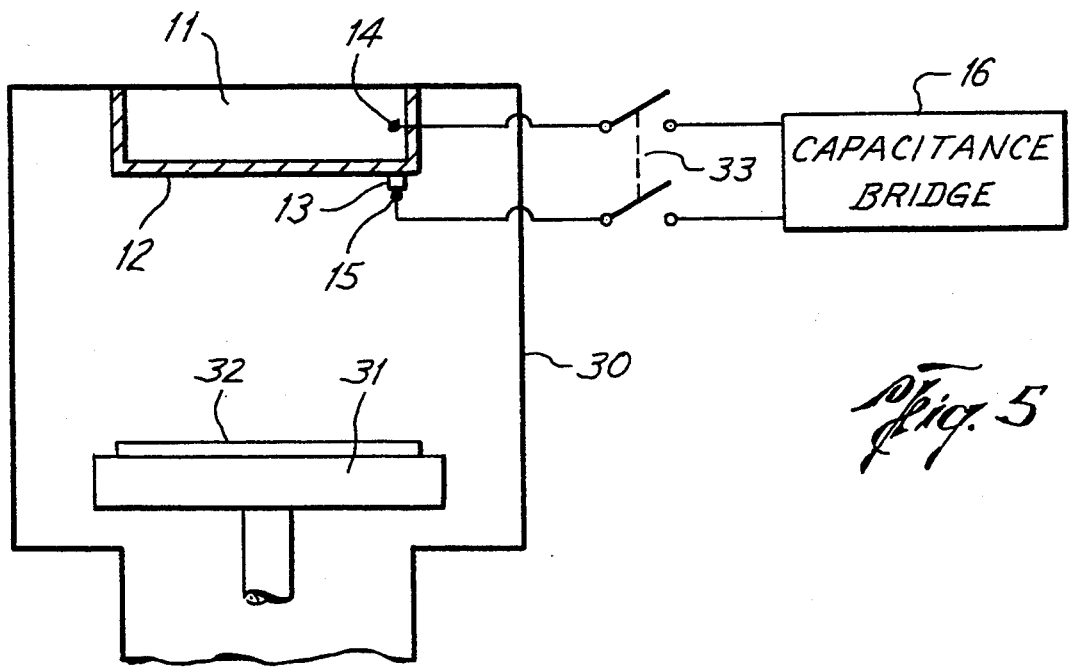
FIG. 5 is a schematic diagram showing the fixture of FIG. 2 in a reactor for an alternative method of practicing the present invention.

Although the practice of the present invention, as noted above, is primary for predicting coating performance, the practice can be readily adapted for providing in-situ measurements during an actual processing cycle. Referring to FIG. 5, the fixture 11 of FIG. 2 is installed within an etching reactor 30. As shown, a wafer platen (wafer chuck) 31 is located within the reactor 30, upon which a semiconductor wafer 32 resides thereon. As shown in FIG. 5, fixture 11 is a "shower head", located at the upper portion of the reactor 30 and utilized for the diffusion of gases entering the reactor 30.

The counter-electrode 13 and the electrical connections 14 and 15 are equivalent to that of FIG. 2. However, the leads from the terminals 14 and 15 are coupled externally to the reactor 30 to the capacitance bridge 16 through switch 33. The switch 33, when closed couples the capacitance bridge 16 to the fixture 11 for taking dissipation factor measurements. Thus, the dissipation factor measurements can be taken without removing the fixture 11 from the reactor.

Between etching cycles, or at other periodic intervals, dissipation factor readings can be taken and the new reading can be compared to a benchmark. Alternatively, such readings can be compared to historical data for the particular fixture to evolve a trend chart to identify any deterioration of the coating over time for that fixture. By such in-situ measurements, potential failures can be predicted and periodic monitoring assesses the prediction. Again, it is essential to have fairly similar environmental conditions within the reactor when these readings are taken in order to obtain consistently uniform readings of the dissipation factor for comparison purposes.

Thus, a technique for predicting performance of an anodic coating on a fixture or a tool based on its dissipation factor is described. It is appreciated that although this prediction is based on the dissipation factor, other circuit parameters for determining the phase angle of response of the coating, such as the power factor, can be readily substituted. Furthermore, other measuring devices, other than the capacitance bridge described herein, can be utilized to measure the dissipation factor or other phase angle indications.

I claim:

1. A method for determining a performance characteristic of an anodic coating anodized upon a surface by characterizing its dielectric property in order to predict susceptibility for deterioration of its dielectric property when used in an erosive environment over a prolonged period, comprising the steps of:

coupling a measurement device, which measures a phase relationship of an impedance to its resistive and reactive components, across opposing surfaces of said anodic coating in order to measure a phase angle of an impedance across a thickness of said anodic coating;

measuring said phase angle of said impedance of said anodic coating at a set frequency;

characterizing said dielectric property of said anodic coating at said set frequency by determining power dissipation based on said measured phase angle;

comparing said measured phase angle to a set of values corresponding to a performance response of anodic coatings in said erosive environment;

predicting long term performance of said anodic coating in said erosive environment based on said measured phase angle, wherein useful life of said anodic coating is estimated prior to actual deterioration or failure of its dielectric property.

2. The method of claim 1 wherein said phase angle is determined by measuring a dissipation factor for said anodic coating, said dissipation factor being indicative of power dissipation within said anodic coating.

3. The method of claim 2 wherein a capacitance meter is used to measure said phase angle to determine said dissipation factor.

4. The method of claim 1 wherein said phase angle is determined by measuring a power factor for said anodic coating, said power factor being indicative of power dissipation within said anodic coating.

5. A method for determining a performance characteristic of an anodic coating anodized upon a surface by characterizing its dielectric property in order to predict susceptibility for deterioration of its dielectric property when used in an etching environment over a prolonged period, comprising the steps of:
 coupling a capacitive measurement device, which measures a phase relationship of an impedance and its capacitive component, across opposing surfaces of said anodic coating in order to measure a phase angle of an impedance across a thickness of said anodic coating;
 measuring said phase angle of said impedance of said anodic coating at a set frequency;
 characterizing said dielectric property of said anodic coating at said set frequency by determining power dissipation based on said measured phase angle;
 comparing said measured phase angle to a set of values corresponding to a performance response of anodic coatings in said etching environment;
 predicting long term performance of said anodic coating in said etching environment based on said measured phase angle, wherein useful life of said anodic coating is estimated prior to actual deterioration or failure of its dielectric property.

6. The method of claim 5 wherein said phase angle is determined by measuring a dissipation factor for said anodic coating, said dissipation factor being indicative of power dissipation within said anodic coating.

7. The method of claim 6 wherein said dissipation factor is also indicative of an erosion rate of said anodic coating when utilized under said etching environment.

8. A method for determining a performance characteristic of an anodic coating anodized upon a surface of a metal fixture by characterizing its dielectric property in order to predict susceptibility for deterioration of its dielectric property when used in an etching environment over a prolonged period, comprising the steps of:
 placing a counter-electrode onto an exposed surface of said anodic coating in order to provide an effective electrical contact to said anodic coating;
 coupling a first electrical lead to said counter-electrode and a second electrical lead to said fixture, wherein providing an effective electrical contact across a thickness of said anodic coating;
 coupling a capacitive measurement device, which measures a phase relationship of an impedance and its capacitive component, across said first and second electrical leads in order to measure a phase angle of an impedance across said thickness of said anodic coating;
 measuring said phase angle of said impedance of said anodic coating at a set frequency;
 characterizing said dielectric property of said anodic coating at said set frequency by determining power dissipation based on said measured phase angle;
 comparing said measured phase angle to a set of values corresponding to a performance response of anodic coatings in said etching environment;
 predicting long term performance of said anodic coating in said etching environment based on said measured phase angle, wherein useful life of said anodic coating is estimated prior to actual deterioration or failure of its dielectric property.

9. The method of claim 8 wherein said phase angle is determined by measuring a dissipation factor for said anodic coating, said dissipation factor being indicative of power dissipation within said anodic coating.

10. The method of claim 9 wherein said dissipation factor is also indicative of an erosion rate of said anodic coating when utilized under said etching environment.

* * * * *

UNITED STATES PATENT AND TRADEMARK OFFICE
CERTIFICATE OF CORRECTION

PATENT NO : 5,410,256
DATED     : April 25, 1995
INVENTOR(S): Janda K.G. Panitz

It is certified that error appears in the above-identified patent and that said Letters Patent are hereby corrected as shown below:

Column 3, line 52, after "Thus" insert --,--.

Column 4, line 26, delete "because".

Column 5, line 57, after "coating," insert --the--.

Column 8, line 4, "primary" should be --primarily--.

Signed and Sealed this

Twelfth Day of August, 1997

Attest:

BRUCE LEHMAN

Attesting Officer

Commissioner of Patents and Trademarks